US006954066B2

(12) United States Patent
Siess et al.

(10) Patent No.: US 6,954,066 B2
(45) Date of Patent: Oct. 11, 2005

(54) ABNORMAL PRESSURE DETERMINATION USING NUCLEAR MAGNETIC RESONANCE LOGGING

(75) Inventors: Charles Preston Siess, Conroen, TX (US); Pavel Syngaevsky, Houston, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 0 days.

(21) Appl. No.: 10/817,422

(22) Filed: Apr. 1, 2004

(65) Prior Publication Data

US 2005/0030020 A1 Feb. 10, 2005

Related U.S. Application Data

(60) Provisional application No. 60/459,490, filed on Apr. 1, 2003.

(51) Int. Cl.[7] .................................................. G01V 3/00
(52) U.S. Cl. ........................................ 324/303; 324/306
(58) Field of Search ................................ 324/303, 306, 324/307, 309, 300

(56) References Cited

U.S. PATENT DOCUMENTS

| | | | | |
|---|---|---|---|---|
| 4,728,892 A | * | 3/1988 | Vinegar et al. .............. 324/309 |
| 4,981,037 A | | 1/1991 | Holbrook et al. ......... 73/152.05 |
| 5,389,877 A | | 2/1995 | Sezginer et al. ............. 324/303 |
| 5,923,167 A | | 7/1999 | Chang et al. ................ 324/303 |
| 6,008,645 A | * | 12/1999 | Bowers et al. ............... 324/303 |
| 6,051,973 A | | 4/2000 | Prammer ..................... 324/303 |
| 6,111,408 A | | 8/2000 | Blades et al. ................ 324/303 |
| 6,173,793 B1 | | 1/2001 | Thompson et al. ............ 175/45 |
| 6,204,663 B1 | | 3/2001 | Prammer ..................... 324/303 |
| 6,232,778 B1 | | 5/2001 | Speier et al. ................ 324/303 |
| 6,242,912 B1 | | 6/2001 | Prammer et al. ............ 324/303 |
| 6,242,913 B1 | | 6/2001 | Prammer ..................... 324/303 |
| 6,255,819 B1 | | 7/2001 | Day et al. .................... 324/303 |
| 6,268,726 B1 | | 7/2001 | Prammer et al. ............ 324/303 |
| 6,316,940 B1 | | 11/2001 | Akkurt ........................ 324/303 |
| 6,337,568 B1 | | 1/2002 | Tutunji et al. ............... 324/303 |
| 6,362,619 B2 | | 3/2002 | Prammer et al. ............ 324/303 |
| 6,366,087 B1 | | 4/2002 | Coates et al. ................ 324/303 |
| 6,411,087 B1 | | 6/2002 | Fat et al. ..................... 324/303 |
| 6,446,736 B1 | | 9/2002 | Kruspe et al. ................. 175/40 |
| 6,518,756 B1 | | 2/2003 | Morys et al. ................ 324/303 |
| 6,531,868 B2 | | 3/2003 | Prammer ..................... 324/303 |
| 6,541,969 B2 | | 4/2003 | Sigal et al. .................. 324/303 |
| 6,703,832 B2 | * | 3/2004 | Heaton et al. ............... 324/303 |
| 6,833,699 B2 | | 12/2004 | Galford et al. .............. 324/303 |

OTHER PUBLICATIONS

Donovan et al., Wireline and LWD NMR Applications in Undersaturated Oil Sands in Deepwater US Gulf of Mexico, Paper BBB, SPWLA 42nd Annual Logging Symposium, Jun. 17–20, 2001.

Prammer et al., The Magnetic Resonance While–Drilling Tool: Theory and Operation, SPE 62981, 2000 SPE Annual Technical Conference and Exhibition, Dallas, 2000.

* cited by examiner

*Primary Examiner*—Louis Arana
(74) *Attorney, Agent, or Firm*—Jones Day

(57) ABSTRACT

A method and apparatus for determining abnormal pressure zones of a geologic formation using NMR measurements, preferably for logging-while-drilling applications. In a preferred embodiment, a normal compaction trend is constructed using NMR-derived clay bound water volume (CBW) content for non-consolidated subsurface formations or bulk volume irreducible (BVI) and CBW for consolidated formations versus depth. Deviations from this normal compaction trend are used to indicate the presence of shale sections with higher porosity that directly corresponds to an overpressured top seal or transitional zone.

21 Claims, 13 Drawing Sheets

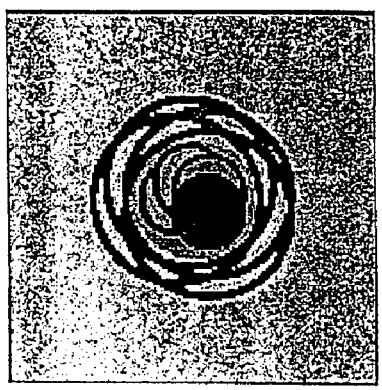
(b)
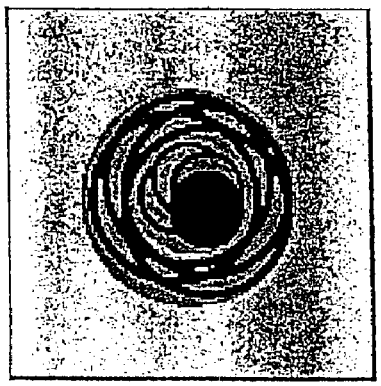
(d)
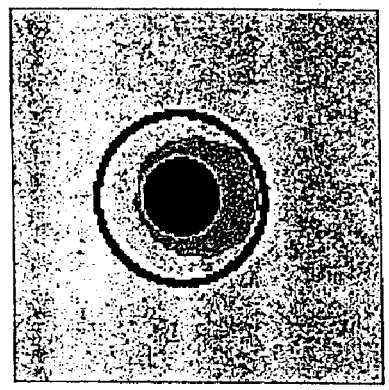
(a)
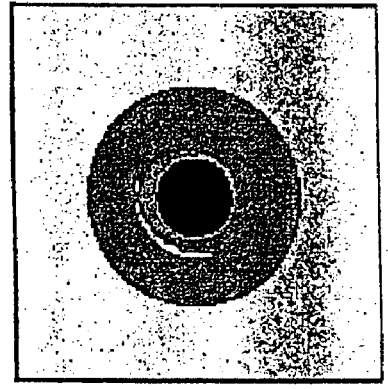
(c)
Fig. 4

| CLAY TYPE | MORPHOLOGY | $T_2$ (ms) or r(μm); | $T_1$ (ms) |
|---|---|---|---|
| Smectite | slurry | ρ=2.3 | 7-60 |
| Smectite | | <1.0 | |
| Illite | slurry | ρ=2.1 | 2-20 |
| Illite | Detrital flakes/sheets | 1-3 | |
| Illite | Grain alteration (rare) | 5-20 μm | |
| Illite | | 1-2 | |
| Chlorite | Grain alteration | 5-20 | |
| Chlorite | Detrital sheet (rare) | ~1-5 μm | |
| Chlorite | Pore lining | 20-40 | |
| Chlorite | | 3-5 | |
| Kaolinite | Pore filling | 5-20 | |
| Kaolinite, Vermiculite | Pore filling | 10-50 | |
| Kaolinite | Grain replacement | 0.3-3 | |
| Kaolinite | slurry | ρ=1.8 | 80-300 |
| Kaolinite | | 4-16 | |
| Glauconite | slurry | ρ=3.3 | 7-25 |
| Ca/Na Montmorillonite | hydrated | 1.7-3 | |
| Illite, kaolinite, chlorite | detrital | 0.1-10 | |
| Kaolinite, chlorite | Grain replacement | 2-20 | |

Fig. 11

ABNORMAL PRESSURE DETERMINATION USING NUCLEAR MAGNETIC RESONANCE LOGGING

This patent application claims priority of provisional patent application Ser. No. 60/459,490, filed Apr. 1, 2003, which is incorporated herein by reference.

FIELD OF THE INVENTION

This invention relates generally to abnormal formation pressure determination in a borehole, and more specifically to such abnormality determination using a method and apparatus for making pulsed nuclear magnetic resonance (NMR) measurements of earth formations. Preferred embodiments are directed to abnormal formation pressure determination via NMR-derived porosity, and logging-while-drilling (LWD) or measuring-while-drilling (MWD) applications.

BACKGROUND OF THE INVENTION

Pore and fracture pressures are the major factors affecting the success of drilling operations. If pressure is not properly evaluated, it can lead to drilling problems such as lost circulation, blowouts, stuck pipe, hole instability, and excessive costs. Unfortunately, formation pressures can be very difficult to quantify precisely where unusual, or abnormal, pressures exist. Abnormal pressure is a subsurface condition in which the pore pressure of a geologic formation exceeds, or less frequently is below, the expected hydrostatic formation pressure. Abnormally high formation pressures typically occur when impermeable rocks such as shales are compacted rapidly during their deposition, so that their pore fluids cannot always escape and must then support the total overlying rock column. Such pressures may occur as shallow as a few hundred meters below the surface or at depths exceeding thousands of meters and can be present in shale/sand sequences and/or carbonate sections.

The occurrence of overpressured zones has classically been determined well after the overpressured zone has been drilled, sometimes with disastrous results. Abnormal pressure can cause a well to blow out or become uncontrollable during drilling, resulting in overwhelming increases in drilling/completion costs. Therefore, the earliest possible determination of the presence of abnormally overpressured subsurface(s) is a paramount piece of information that is of acute interest to the drilling engineer and the operating company. In particular, knowledge of formation pressure during the drilling enables the well operator to make preparations such as increasing the weight of the drill mud column in order to maintain well control and to prevent a blow out (or to resist fluid loss), as zones of overpressure (or underpressure) are penetrated by the drill bit.

Generally, as an overpressured formation is approached, there are marked differences in degree of compaction and porosity of various formation layers. Also, differences in the minerals composition of interstitial fluids typically occur, and the formation pressure may begin to rise and approach or even exceed the bottom hole pressure, thus decreasing the bottom hole pressure differential. If properties, which are affected by such factors, are closely monitored and plotted with respect to depth, an abnormally pressured zone may be identified when a distinct deviation from an average line trending with depth is observed. To this end, the most commonly used methods for formation pressure prediction in logging-while-drilling (LWD) utilize the same phenomena: changes in shale porosity due to burial and deviation from "normal compaction" trend in abnormally pressurized zones.

The most commonly used measurement techniques include resistivity and acoustic (sonic) logs that may be supplemented with gamma ray and/or SP (spontaneous potential) as shale indicators. In complex cases, a gamma-gamma density and neutron (pulse-neutron) logs are also used. Typically, such logging-while-drilling techniques are used to: (1) identify shale layers, (2) assess their porosity, and (3) account for possible complications, such as lithology changes due to diagenesis, water salinity variations, natural or drilling-induced fractures. The measured parameters, such as electric (resistivity), acoustic (travel time) and nuclear (gamma-gamma/neutron-gamma/pulsed neutron), are plotted versus depth and an established normal compaction trend is provided. Any deviation from this trend should be recognized on porosity logs and may be associated with a subsurface pressure anomaly.

All conventional logs, however, suffer from one key weakness—estimated total porosity is not lithology-independent. As known, lithology-dependent methods give a correct answer in shales if: (1) the lithology is known; (2) there are no fracture components; and (3) the pore space fluid is pure water. However, uncertainties in matrix composition, such as (1) mixed lithology and diagenetic alteration, (2) changes in pore water salinity (salt influence or fresh-water entrapment), (3) presence of hydrocarbons, and (4) natural/induced fractures cause calculation of formation pressure to become very challenging, if not impossible in complex reservoir cases. Most importantly, all known techniques have failed in cases of variations in water salinity (presence of salt dome) and fracturing (tectonic faulting/drilling damage).

The resistivity-based logging techniques are most effected by variations in matrix mineralogy. In normally pressured shales (hydro-pressure regime), there is a decrease of conductivity with depth of burial, due to compaction and associated porosity and water loss. This decreasing of shale porosity forms a "normal compaction line" trend in conductivity or resistivity versus depth plots. Generally, such a normal compaction line can be established for a given area. Depending on various factors this line may shift right or left, but the slope remains essentially the same. Shale-reading points that fall to the left (higher conductivity area) of the normal compaction line are often associated with zones of abnormally high pressure. However, a basic assumption in the use of resistivity logs is that water salinity in shales remains the same, and therefore resistivity changes could be correlated to actual porosity variations. This assumption becomes invalid if there are variations in salt deposition, which may facilitate or impede water conductivity, thus rendering resistivity-based porosity values incorrect.

The above problem is illustrated in FIG. 1, which is a resistivity log of an overpressured formation from Gulf-of-Mexico area. In the FIG. 1, the normal compaction trend is shown as solid line, and resistivity data as black points. The deviation of resistivity at the depth of 2800 m is associated with increased amount of clay-bound water (hence increased conductivity). In this well, two pressure compartment are identified: ~2500–3200 m and 3400–3800 m. Reasons for this compartmentalization, however, cannot be determined from the resistivity log, since there is no information on the spectral distribution of the total porosity. Reasons for increasing resistivity at 3300 m are unclear also; they may be due to lithology changes, such as presence of dispersed carbonaceous material, diagenetic alterations in shales, or others.

Acoustic logs are also effected by variations in matrix mineralogy. In normally pressured shales sonic logs generally show a decrease in interval transit time with depth of burial. Since interval transit time is a function of porosity, this decrease indicates that the shale porosity decreases with depth. When depth is plotted on the linear y-axis versus shale interval transit time on the logarithmic x-axis, a straight line can be drawn trough the normal pressure points. Points that fall to the left of the normal line represent a zone of abnormally high formation pressure, as shown in FIG. 2. Such acoustic log is less dependent on water conductivity, but strongly influenced by natural and drilling-induced fractures that may drive calculated porosity values too high. Moreover, both acoustic and density methods are strongly influenced by gas presence.

FIG. 2 illustrates acoustic (sonic) log in an overpressured formation from Gulf-of-Mexico area. A normal compaction trend derived from the acoustic log is shown as the smooth line. Deviations to the left are due to increasing of shale porosity and hence are associated with undercompaction in overpressured formations. Top of pressure seal is observed at depth of about 3220 meters, where deviation of actual data points (circles) from the normal trend becomes apparent. Pressure seal is a gradual change in porosity related to pressure increase, also known as transitional zone. Overpressured formation zone marked by constant values in travel time, and started at approximately 4000 meters.

Difficulties associated with the prior art are further related to the fact that often pressure predictions from various conventional logs disagree with each other. FIG. 3, for example, illustrates such disagreement in pore pressure estimates from resistivity and acoustic logs. Logging-while-drilling resistivity measurements (circles) show a long transitional zone in the 9,000–10,000 feet-interval, which is typical for damaged shaly pressure seal. Such a long transitional zone is probably associated with diagenetic alterations and corresponding variations in water salinity. In contrast, acoustic log (small dots in the midsection of the drawing) shows fairly steep changes, meaning that pressure seal is in good condition. Also, fracture gradient (dashed line), calculated based on pore pressure is in disagreement with leak-of test results (EMW—equivalent mud weight) line. Moreover, below 11000 feet calculations based on resistivity seriously overestimates formation pore pressure.

Therefore, it is an object of the present invention to develop a method and system for real-time analysis of shales and accurate porosity-based formation pressure estimation to facilitate early warning of the existence of overpressure. In particular, it is desirable for the new method to enable lithology-independent porosity measurements—that is, at least a portion of the extracted data is related only to shale micro-porosity, wherein diagenetic changes associated with shale composition are not interfering with the desired data. Additionally, it is desirable that at least a portion of the data can provide other information about a reservoir or shale zone. Additionally, it is desirable for the system to have mechanical strength and measurement sensitivity to withstand shock, vibration and erosion associated with drilling and to enable logging and measurement while drilling of the underground formation in most complex underground conditions.

SUMMARY OF THE INVENTION

To this end, in one aspect the invention is a nuclear magnetic resonance (NMR)-based method and system for real-time analysis of geologic formations including accurate porosity-based formation pressure estimation. In particular, the method and system of the present invention effectively resolve problems associated with prior art logging techniques discussed above. NMR's unique ability to discriminate porosity associated with clay-bound, capillary-bound and free fluid volumes allows the user to extract the signal only from shaly section and ignore the presence of "additional" porosity from induced fracturing or presence of silty sandstone material. Moreover, changes in pore water salinity are do not affect NMR measurements, and hydrocarbon signal can be recognized and accounted for using changes in the hydrogen index (HI) parameter. In general, since NMR logging used in accordance with the present invention is lithology-independent, it is not effected by matrix variations and provides accurate porosity estimation in mixed or even unknown matrix composition.

In particular, it has been recognized by the present inventors that $T_1$ (longitudinal polarization time) measurements are especially effective for while drilling measurement of porosity. U.S. Pat. No. 6,051,973, the entire contents of which is incorporated herein by reference, describes a method of obtaining reservoir information based on $T_1$ measurements. Unlike the $T_2$ measurements that are sensitive to magnetic field changes (which may result, for example, from movement of the logging tool) and its associated dephasing effects, the $T_1$ polarization process is substantially immune to small field fluctuations characteristic to logging-while-drilling operations. In a preferred embodiment of the invention, these motion-insensitive $T_1$ measurements are used as a primary source of spectral porosity associated with clay- and capillary-bound water. Since an excessive porosity value characterizes shales in or overlying overpressured zones, these overpressured zones can be recognized using $T_1$ measurements.

Fundamentally, the proposed NMR approach utilizes the same principle as conventional porosity logs to provide advance identification of overpressure; namely, the overpressured subsurface shale intervals contain higher volumes of water within versus shale intervals following normal pressure trends. However, in accordance with a preferred embodiment, the method of the present invention provides an additional benefit of discriminating between total pore space volume, Free Fluid volume (FFI), Capillary Bound Water volume (BVI) and Clay Bound Water volume (CBW) of subsurface layers, while drilling the physical well. In accordance with one aspect of the invention, the direct continuous measurement of clay-bound water during the drilling process serves as definitive indication that an overpressured zone has been entered.

Accordingly, in a preferred embodiment, a method for determining abnormal pressure zones of a geologic formation is disclosed. In particular, in a preferred embodiment, a normal compaction trend is constructed using NMR-derived CBW content for non-consolidated formations or CBW and BVI for consolidated subsurface formations versus depth. Then, any deviations from this normal compaction trend are determined using one of the industry-accepted techniques. Such deviations indicate a presence of shale sections with higher porosity that directly corresponds to an overpressured top seal or transitional zone.

In accordance with different embodiments of the invention, various techniques may be used to determine pressure deviations from the normal compaction trend. Such known techniques are described, for example, by (1) Hottmann et al. in "Estimation of Formation Pressures From Log-Derived Shale Properties," JPT (*Journal Petroleum Technology*) June, 1965; (2) Eaton in "The Equation for Geopressure Prediction From Well Logs," paper SPE 5544, 1975 Annual Technical Conference, Dallas Sep. 28–Oct. 1, 1975; (3) Rasmus et al. "A Framework To Estimate Pore Pressures in Real-Time," February 1990, Measurement-While-Drilling Symposium, Louisiana State University, Baton Rouge, La.; (4) Holbrook et al. in "A Petrophysical/Mechanical Mathematical Model for Real-Time Wellsite Pore-Pressure/Fracture-Gradient Prediction," Paper SPE 16666 presented at the 1987 SPE Annual Technical Conference, Dallas, Tex., September 1987; and (5) Bryant in "A Dual Shale Pore Pressure Detection Technique," paper SPE 18714 presented at the 1989 SPE/IADC Drilling Conference, New Orleans, La. February –March 1989. All of the above papers are incorporated herein by reference. Each technique can be readily modified by one of ordinary skill in the art, with the benefit of this disclosure, to utilize the NMR-derived bound water porosity in shales to provide an estimate of pore pressure in the shale and in a more permeable zone below the shale.

For example, resistivity is often utilized to calculate water porosity. In normally pressured shales (hydro-pressure regime), there is a decrease of conductivity with depth of burial, due to compaction and associated water loss, that is, loss of presumably bound water due to decreasing porosity. This decreasing of shale porosity forms a "normal compaction line" trend. Generally, such "normal line" can be established for a given area, depending on various factors this line may shift right or left, but the slope remains essentially the same. Shale-reading points that fall to the left (higher conductivity area) of the normal compaction line are zones of abnormally high pressure. Step-by-step procedure for applying the resistivity approach is described, for example, by Matthewes W. R., and Kelly, J. "How to predict formation pressure and fracture gradient," The Oil and Gas Journal, February 1967, the contents of which is incorporated by reference. Utilizing NMR-based bound water in such a method is straightforward, and has an advantage over the prior art in that salinity variations, fractures, and the like which may give misleading information from resistivity logs will not be apparent in the NMR-based porosity data.

In normally pressured shales sonic (travel time) logs shows a decrease in interval transit time with depth of burial. Sonic logs are typically utilized to estimate porosity of a formation. Since interval transit time is a function of porosity, a decrease in time is associated with shale porosity decreasing with depth. When depth is plotted on a linear Y-axis versus shale interval transit time on the logarithmic X-axis, a straight line can be drawn trough the normal pressure points. Points that fall to the left of the normal line are zone of abnormally high formation pressure. See SPE paper 62981, October 2000, and SPWLA paper BBB, June 2001, which are incorporated herein by reference. This approach is less dependent on water conductivity, but strongly influenced by natural and drilling-induced fractures that may drive calculated porosity values too high.

In a preferred embodiment, a method for while-drilling measurement of the formation pressure is based on bound water determinations from motion insensitive $T_1$ (longitudinal polarization time) recovery process as the primary source of spectral porosity data. In another embodiment, the spectral porosity is determined from the $T_2$ logging-while drilling measurement. In yet another embodiment, the $T_1$ data from wireline logging tool is used to estimate formation pressure. In still another embodiment, $T_2$ data from the wireline NMR logging tool is utilized to determine spectral porosity. In yet another embodiment, spectral porosity from both insensitive $T_1$ and from the $T_2$ data is collected, wherein $T_1$ data is obtained from logging-while drilling measurements and the $T_2$ data is collected either by logging-while drilling measurements or by wireline logging or by both in combination. In yet another embodiment, spectral porosity from both insensitive $T_1$ data are collected, wherein $T_1$ data is obtained from logging-while drilling measurements, and this data is combined with one or more of $T_2$ data, sonic log data, and/or resistivity log data, all of which are beneficially collected by logging-while drilling. The data is interpreted to deduce increases in the water content of shales, which increases are indicative of abnormal pressure. In preferred embodiments of the above described methods, the data is automatically interpreted and the driller is advised of the probability of abnormal pressure substantially in real time, as the NMR logging tool enters the shale. Since NMR is a substantially lithology-independent measurement, the presence of various minerals associated with shale diagenesis or change in facies that adversely affect prior art methods of determining shale porosity will effect neither $T_1$ nor $T_2$ data obtained in accordance with the present invention.

The method(s) used in accordance with this invention may be used to enable: (1) detection of the top of overpressure formations at the early stages of formation penetration, and (2) application of necessary changes to drilling program and casing design in real-time. In particular, unlike any other known logging method (e.g., resistivity, acoustic, density), the real-time $T_1$ measurements enable handling of complex reservoir conditions including salt proximity, fracturing associated with faulting and mixed rock lithology. Notably, the disclosed method(s) and system are extremely valuable in the areas where a shallow gas presence may cause significant drilling accidents (e.g., Gulf-of-Mexico, North Sea, Caspian Depression basins etc.).

BRIEF DESCRIPTION OF THE DRAWINGS

This invention may best be understood with reference to the attached drawings, in which:

FIGS. 4A–4D illustrate the impact of drilling on the NMR measurements. In particular, FIG. 4A is a schematic cross-section diagram of a NMR tool in a borehole showing the sensitive region as a circle around the tool within the borehole. FIG. 4B illustrates the effect of lateral tool movement on the sensitive region. FIG. 4C shows magnetization as result of a saturation pulse. FIG. 4D shows the effect of lateral tool motion on the readout sequence following the saturation pulse.

FIG. 11 presents published data on $T_{2cut-off}$ values to separate CBW and effective porosity.

DETAILED DESCRIPTION OF THE PREFERRED EMBODIMENTS

Figure 1:
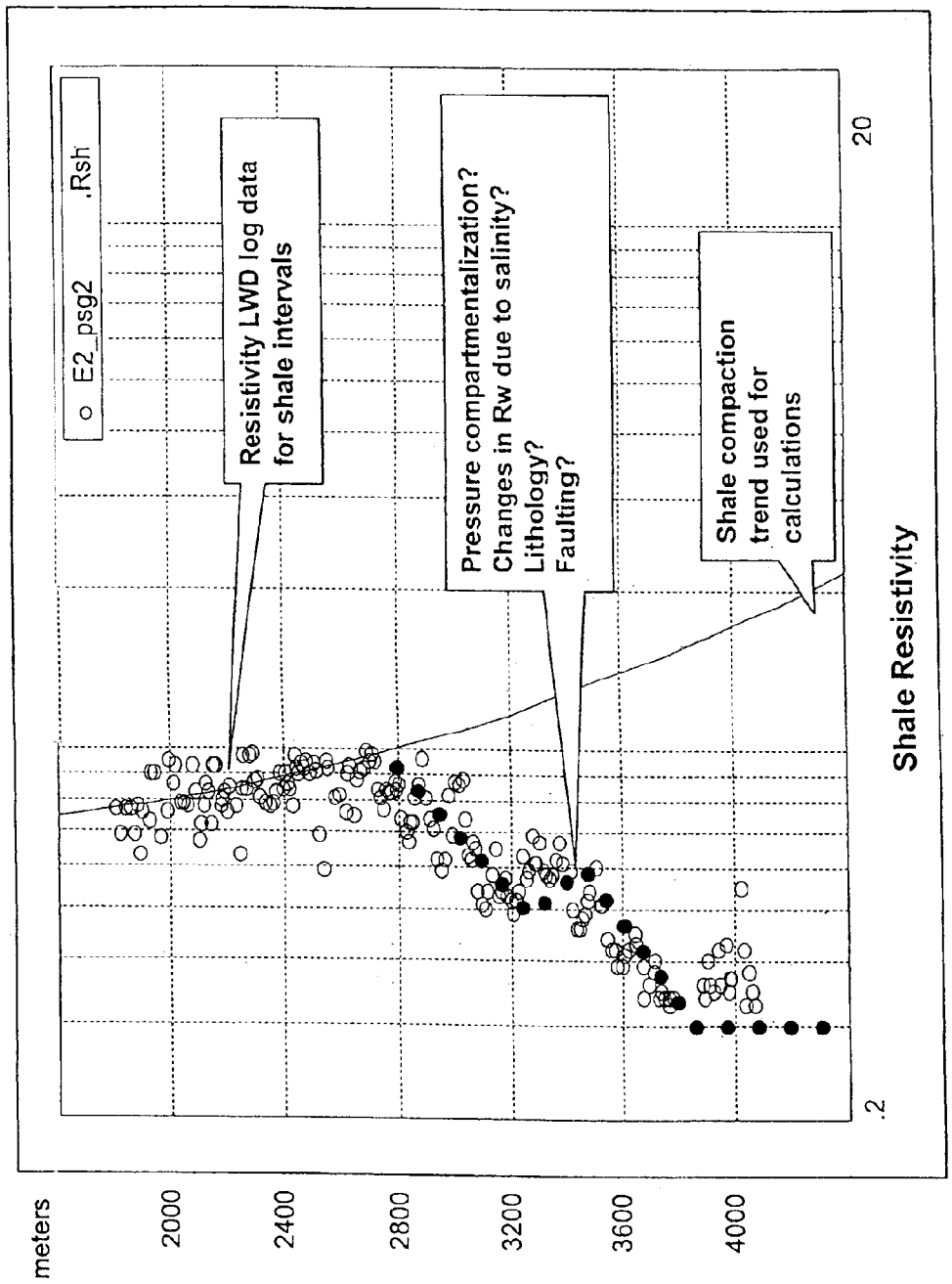
FIG. 1 is a plot of normal compaction trend and resistivity LWD data versus depth for shale intervals.
Figure 2:
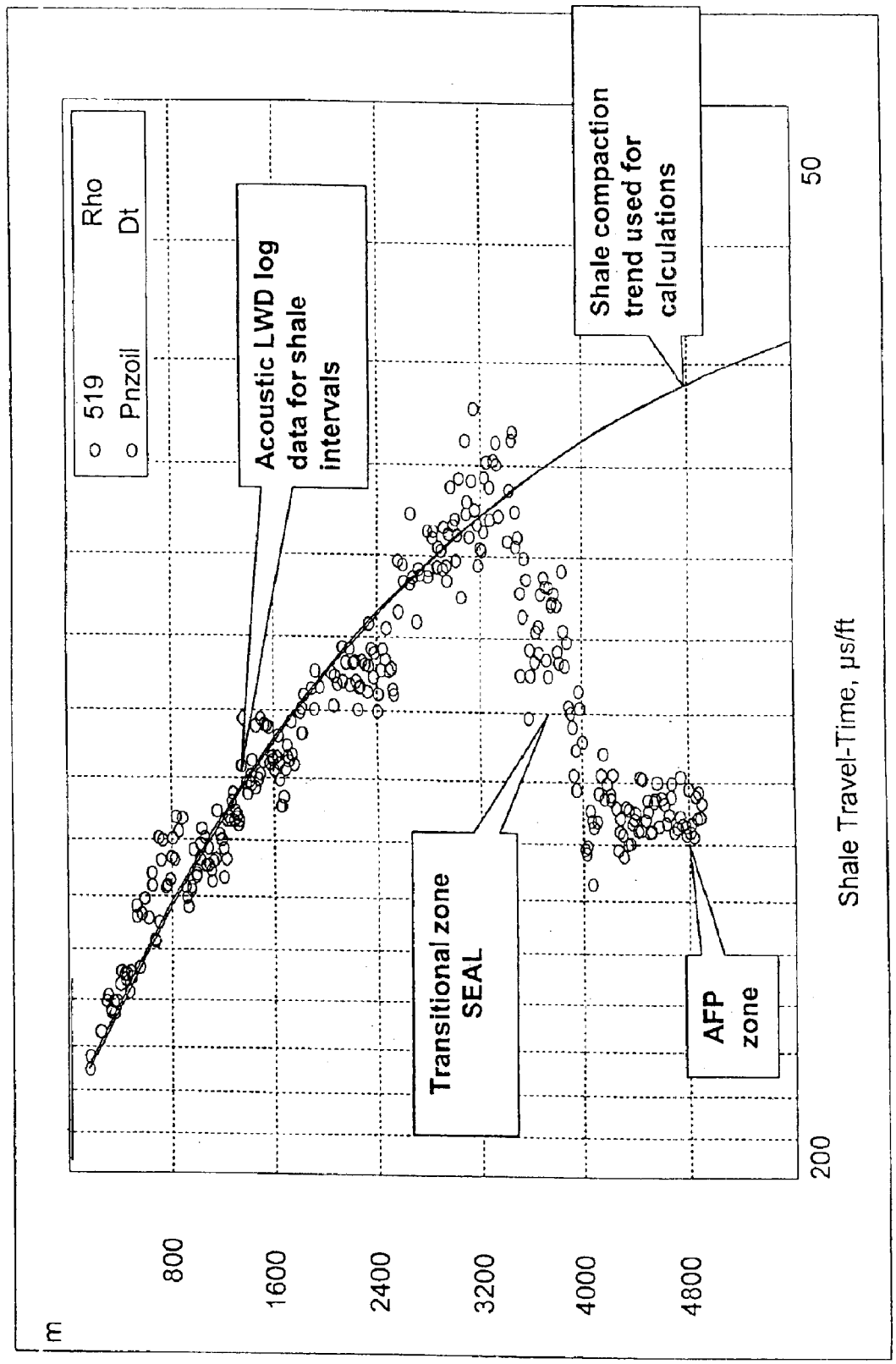
FIG. 2 is a plot of normal compaction trend and acoustic LWD data versus depth for shale intervals.
Figure 3:
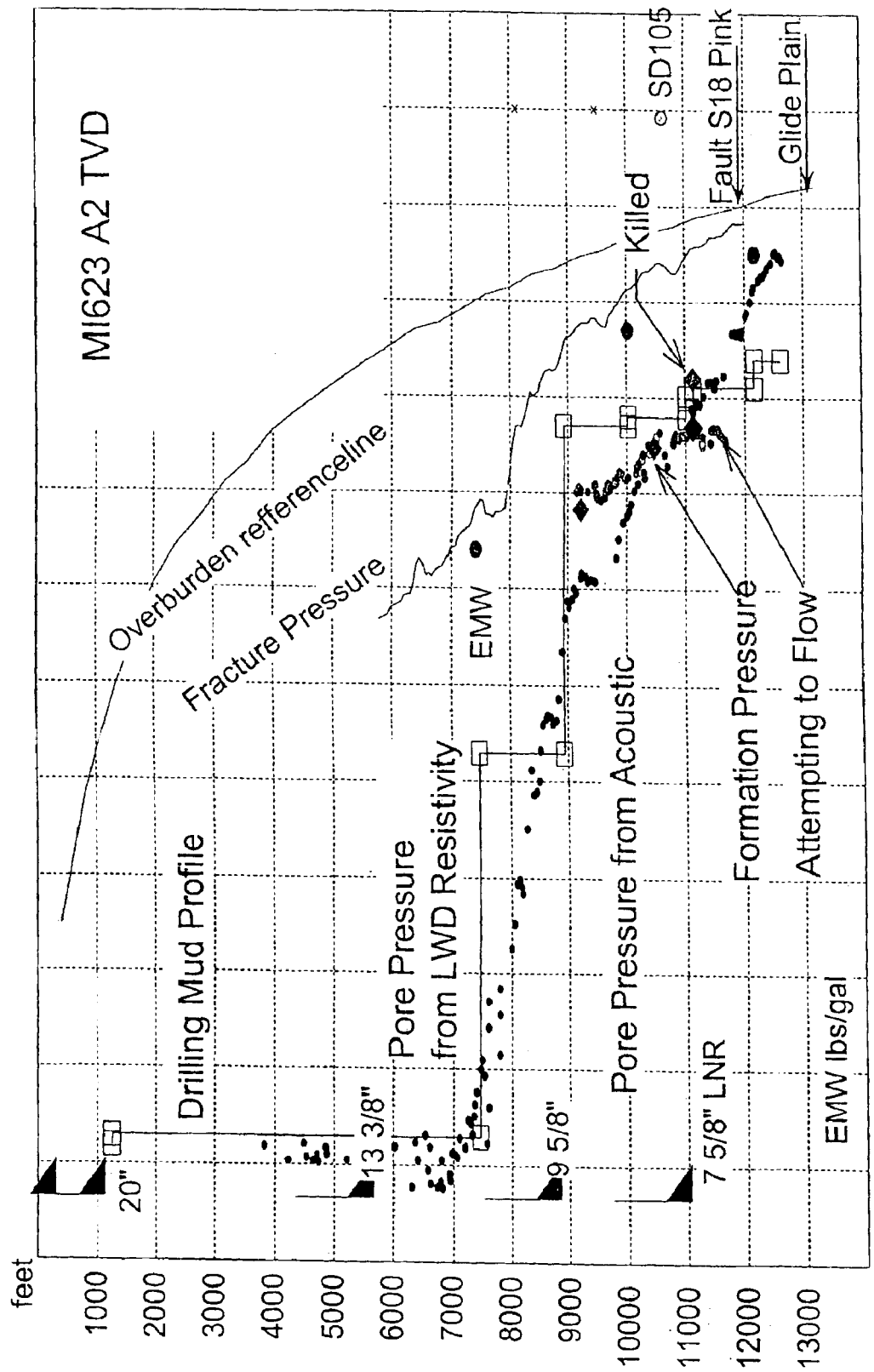
FIG. 3 is a comparison of resistivity LWD data and acoustic LWD data from the same well.

Section A below describes the preferred embodiments of the method(s) used in accordance with this invention for the NMR-based porosity measurement and subsequent abnormal formation pressure determination. Section B discusses pore pressure determination from NMR data. Section C describes an example embodiment of a NMR LWD tool suitable for in situ abnormal pressure determination in accordance with the invention. For a comprehensive review of the NMR technology, including logging methods and various tool designs, the interested reader is directed, for example, to the book by Coates et al. entitled "NMR Logging: Principles and Applications" distributed by Gulf Publishing Company, and incorporated in its entirety by reference for background.

(A) Porosity from NMR Data

It is well known in the field of NMR measurements of earth formations surrounding a borehole to use a downhole static magnetic field $B_0$ to align the magnetic moment of spinning hydrogen ($H^{2+}$) protons in the formation in a first direction, the direction of the static magnetic field $B_0$. In order to establish equilibrium, the hydrogen protons must be exposed to the polarizing field for a multiple of the characteristic relaxation time $T_1$. Then, the magnetic component of a radio frequency (RF) electromagnetic wave pulse, which is polarized in a second direction orthogonal to the static field $B_0$, is used to tip the protons to align them in a direction that is orthogonal to both the first and the second direction. This initial RF pulse is thus called a 90° pulse.

Following the 90° pulse, the protons in the formation begin to precess about the axis of the first direction. As a result, the protons produce an oscillating magnetic field. However, due to inhomogeneities in the static magnetic field and irreversible molecular processes, the protons begin to de-phase, which causes the induced signal to decay. Nevertheless, the dephasing due to inhomogeneities in the static magnetic field is partially reversible. Therefore, by applying a 180° RF pulse, the instantaneous phases are reversed such that the protons gradually come back into phase, thus rebuilding the induced signal. After the signal peaks at the time when the protons are back in phase, the signal will then begin to decay due to dephasing in the opposite direction. Thus, another 180° RF pulse is needed to again reverse the instantaneous phases and thereby rebuild the signal. By repeating a series of 180° RF pulses, the signal is periodically rebuilt after each dephasing, although each rebuilding is to a slightly lesser peak amplitude due to the irreversible molecular processes. This sequence is known in the art as the Carr-Purcell-Meiboom-Gill (CPMG) pulse sequence. Each rebuilding of the signal in this manner is called a spin echo, and the time constant associated with the decay of the spin echo amplitudes is called the transverse relaxation time, $T_2$. Eventually, the irreversible processes prevail, such that no further rephasing is possible and the signal dies out completely.

In wireline logging, NMR-derived porosity is traditionally based on $T_2$ measurements. Notably, it was shown by Kleinberg et al. in "Nuclear Magnetic Resonance of Rocks: $T_1$ vs. $T_2$," paper SPE 26470, presented at the 68th Annual Technical Conference and Exhibition of the Society of Petroleum Engineers, Houston, Tex., Oct. 3–6, 1993, that relaxation time measurements entirely based on $T_1$ are not suitable for a moving wireline tool. But in accordance with the present invention this conventional understanding is challenged, and significant benefit is derived by using NMR relaxation time measurements determining longitudinal relaxation times $T_1$, instead of transversal relaxation times $T_2$ that are typically used by a wireline tool. In particular, the method(s) of this application take advantage of the magnetic field gradient, which can be approximated in the proximity of the sensitive volume as a linear fall-off of the magnetic field strength (and also of NMR resonance frequency) in the radial direction. Compared to $T_2$ measurements, $T_1$ acquisitions are more time consuming and limit logging speeds to 1–3 ft/min. For LWD, however, this speed limit agrees well with the maximum rates of penetration (ROPs) to be expected (also 1–3 ft/min.). The inherent robustness of a $T_1$ measurement makes it a preferred vehicle in accordance with this application for a while-drilling measurement of porosity and free-fluid volume.

One problem with $T_2$ measurements is that they are adversely effected by typical lateral and vertical tool motions that occur during logging-while-drilling operations. FIGS. 4A–4B illustrate the impact of drilling on a regular data acquisition: as seen from above, the sensitive volume of the tool randomly moves with the tool motion. FIG. 4A shows a schematic cross section of the NMR tool in a borehole. The sensitive region is a cylinder around the tool within the formation. A $T_2$ pulse/measurement sequence started at any given point in time does not stay focused on a specific measurement volume. FIG. 4b shows how random lateral tool movement displaces the sensitive region within the duration of a regular CPMG pulse sequence (100–500 ms). Consequently, the returned echo amplitudes appear to decay much faster compared to a static measurement. A simple bound fluid vs. free fluid determination requires at least 100 ms measurement time. Given average lateral velocity and displacement conditions, the combined affects of dephasing and loss of measurement volume act to suppress the echo amplitudes within a few tens of milliseconds.

Unlike $T_2$ measurements, which are sensitive to magnetic field changes and the associated dephasing effects, the $T_1$ recovery process is immune to small field fluctuations caused by lateral motion of the tool during drilling. FIGS. 4c–4d illustrate $T_1$ relaxation model. As shown in FIG. 4c, the $T_1$ relaxation mechanism is characterized by saturation pulse that zeros nuclear magnetization within a large volume (e.g. 30 cm in radius) shown as a gray band in FIGS. 4c and 4d. Then, after a variable recovery time period that allows polarization of protons in the volume of the formation exposed to the magnetic field, the build-up of magnetization is monitored by fast readout sequences. Since the saturated volume of the formation is large compared to the lateral motion of the tool, the readout sequence is unaffected by the lateral tool motion. Accordingly, in a preferred embodiment of the invention, $T_1$ relaxation spectra is used to derive formation porosity because $T_1$ reflects the intrinsic relaxation mechanisms with a minimum of instrumentation artifacts.

Finally, in accordance with the present invention the produced $T_1$ relaxation curve is used to derive petrophysical properties of the formation or shale, as known in the art. In particular, the resultant $T_1$ relaxation curve is processed to extract the dominant $T_1$ relaxation modes, from which amounts of bound water, free water and hydrocarbons are estimated. The characteristic $T_1$ times of the surface-wetting phase can also be used to estimate formation pore size distributions and formation permeability, especially in sandstone.

The petrophysical model for $T_1$-based porosity is described next. The NMR-measured total porosity is defined as $$\phi_{NMRA} = \frac{M_0}{M_{100\%}(0)},$$

where $M_{100\%}(0)$ is the measured magnetization for 100% bulk water with the same sensitive volume and $M_0$ is the macroscopic net magnetization. The following equation defines a relationship between the longitudinal relaxation time $T_1$ and the magnitude of magnetization $M_z$ along the z axis, when protons are exposed to the $B_0$ field for time $T_w$:

$$M_z(T_w) = M_0\left(1 - e^{\frac{-T_w}{T_1}}\right).$$

To avoid underestimating $M_0$, full polarization or nearly full polarization (95%) is desired. To achieve 95% polarization, $T_w$ should be equal to three times $T_1$. It should be noted that the longitudinal relaxation time $T_1$ has two components given by the expression:

$$\frac{1}{T_1} = \frac{1}{T_{1B}} + \frac{1}{T_{1S}},$$

where $T_{1B}$ and $T_{1S}$ are the corresponding B—bulk and S—surface components. In shales that are used for abnormal pressure characterization only surface component are typically present, and $T_1$ could be expressed as:

$$\frac{1}{T_1} = \frac{1}{T_{1S}} = \rho_1\left(\frac{S}{V}\right)_{PORE},$$

where $\rho$ is the surface relaxivity and S/V is surface-to-volume ratio of pore system.

Two data acquisition modes are developed using the petrophysical model for the $T_1$-based porosity. The first mode is called $T_1$-Logging ($T_1$); it is best suited for while-drilling operations because of low sensitivity to lateral and vertical tool motion. The second mode used in specific embodiments is $T_2$-Logging ($T_2$). It closely matches wireline logging (e.g., MRIL-Prime™ tool, available from Halliburton Energy Services, Inc., Houston, Tex.) and thus is more suitable for sliding, wiping and tripping measurements. In accordance with a specific embodiment, either a logging-while-drilling or wireline tool may be used to acquire NMR data using these two modes. Preferably, the logging tool will alternately switch between the $T_1$ and $T_2$ modes. The transition between the data acquisition modes may be triggered, for example, by elapsed time, by counting measurements, or can be tied to the outputs of accelerometers/magnetometers that distinguish drilling and non-drilling conditions. For instance, the while-drilling tool may be programmed to continuously toggle back and forth between the $T_1$ and $T_2$ modes. In postprocessing, drilling and non-drilling periods can be identified and the invalid $T_2$ data recorded during drilling can be discarded.

Table 1 summarizes the data acquisition parameters for the wireline tool (using the MRIL-Prime™ as base comparison), for the $T_1$ mode (while-drilling logging) and $T_2$ mode (after-drilling logging). $T_2$ parameters closely resemble those of a wireline tool, except for slightly lower frequencies, field gradients and lower logging speeds. $T_2$ speeds should be preferably limited to about 300 ft/hr if hydrocarbon typing (i.e., gas detection) is a logging objective.

TABLE 1

Comparison of Tool Parameters for MRIL-Prime ™, MRI-LWD in $T_1$ mode, and MRI-LWD in $T_2$ mode

| Tool parameters | MRIL-Prime ™ wireline | MRI-LWD $T_1$ mode | MRI-LWD $T_2$ mode |
| --- | --- | --- | --- |
| Frequency Range | 580–750 kHz | 500 kHz | 580–750 kHz |
| Frequency Spacing (min) | 12 kHz | N/A | 12 kHz |
| No. of Frequencies (max) | 9 | 1 | 2 |
| Field Gradient | 17–32 G/cm | 14 G/cm | ~14 G/cm |
| Echo Spacing (min) | 0.5 ms | 0.5 ms | 0.5 ms |
| Measurement Mode | $T_2$ | $T_1$ | $T_1$ and $T_2$ |

Figure 5:
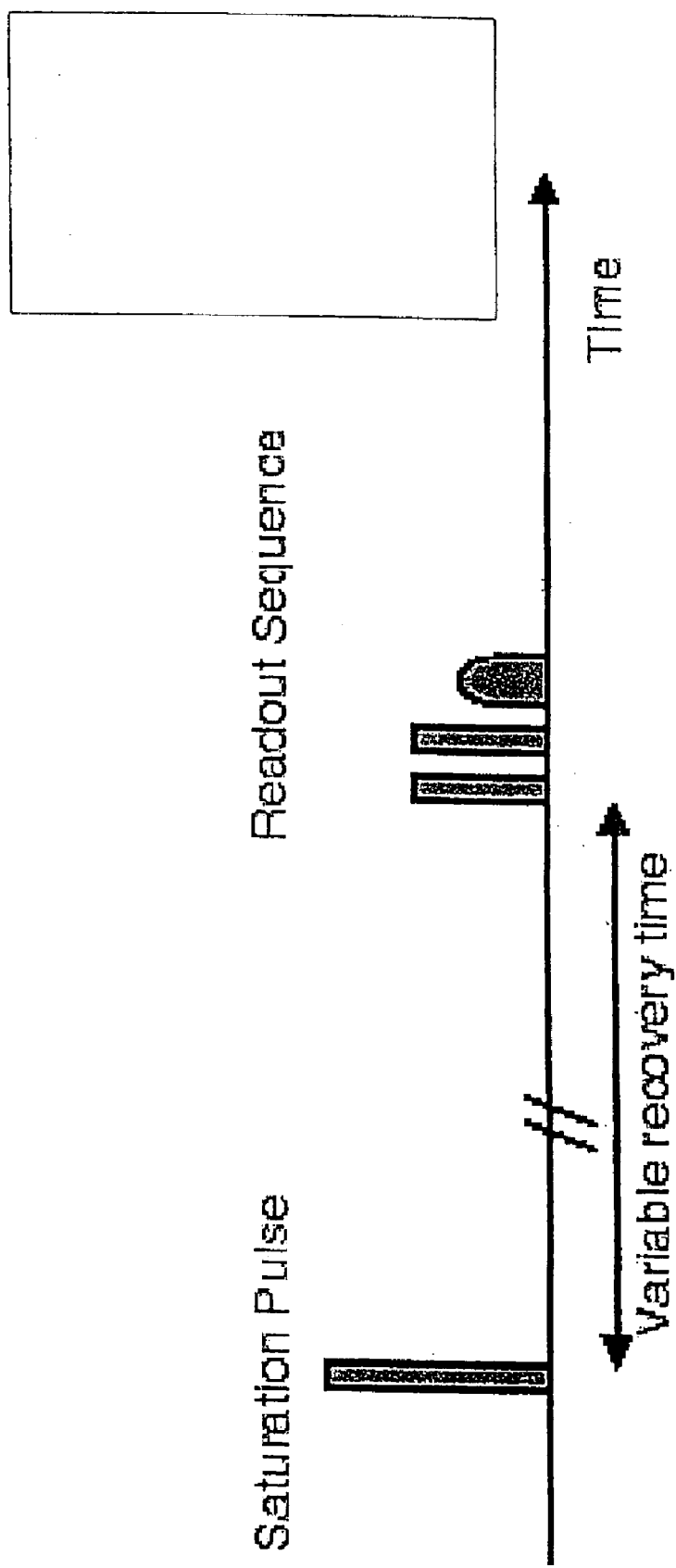
FIG. 5 illustrates an example pulse sequence in accordance with a preferred embodiment.

The $T_1$ log ($T_1$) used in a preferred embodiment is robust against typical lateral and vertical tool displacement due to its reliance on $T_1$ measurements. FIG. 5 illustrates the preferred mode for data acquisition during drilling based on a $T_1$ recovery mechanism. The pulse diagram in FIG. 5 starts with a saturation pulse. This pulse reaches a large volume (gray band in FIGS. 4c and 4d). The nuclear magnetization is instantly zeroed within this band during the pulse, and then allowed to recover to its equilibrium condition. After a timed recovery delay, a readout sequence consisting of two pulses and a single echo acquisition converts the recovered magnetization into an amplitude-modulated signal. The readout takes only 0.5 ms, which is short enough to suppress dephasing effects. Equally important, the signal beneficially comes from a thin-walled cylinder (about 1 mm thick). As long as this cylinder is contained in the much larger volume reached by the saturation pulse, the measurement is valid. The sequence is preferably repeated with variable recovery times, i.e., 1, 3, 10, 30, 100, 300, 1000 and 3000 ms. This allows various treatments of the data collected, which can provide different information as needed.

In another embodiment, a method of obtaining $T_1$ measurements comprises the steps of generating at least one radio frequency pulse covering a relatively wide range of frequencies to saturate the nuclear magnetization in a cylindrical volume around the tool; transmitting a readout pulse at a frequency near the center of the range of covered frequencies, the readout pulse following a predetermined wait time; applying at least one refocusing pulse following the readout pulse; receiving at least one NMR echo corresponding to the readout pulse; repeating the above steps for a different wait time to produce a plurality of data points on a $T_1$ relaxation curve; and processing the produced $T_1$ relaxation curve to derive petrophysical properties of the formation.

In another embodiment, NMR data can be obtained by, for example, the method described in U.S. Pat. No. 6,232,778, the contents of which are incorporated herein by reference. NMR measurements, in general, are accomplished by causing the magnetic moments of nuclei in a formation to precess about an axis. The axis about which the hydrogen nuclei precess may be established by applying a strong, polarizing, static magnetic field to the formation, such as through the use of permanent magnets. This field causes the proton spins to align in a direction parallel to the applied field (this step, which is sometimes referred to as the creation of longitudinal magnetization, results in the nuclei being "polarized"). Polarization does not occur immediately, but instead grows in accordance with a time constant $T_1$, and may take as long as several seconds to occur. After sufficient time, a thermal equilibrium polarization has been established. The U.S. Pat. No. 6,232,778 patent discloses methods for determining the bound fluid volume of a formation utilizing nuclear magnetic resonance (NMR) techniques in which less than full polarization occurs and in which less than a complete NMR distribution is acquired. The effect of the polarizing static magnetic field is shortened in time by applying a shortened wait time between NMR measurements so that only the bound fluid of the formation is polarized. The shortened wait time is effectuated by early application of the oscillating magnetic field to the formation which, in conjunction with a limited number of refocusing pulses, induces signals in the formation that are measured by the NMR tool. The peak amplitudes of these signals corresponds to the clay-bound and free-fluid volumes.

In accordance with a preferred embodiment, the primary data record in $T_1$ mode is a series of echo amplitudes associated with increasing recovery times and therefore of monotonically increasing amplitude. It is possible to collect more than one echo per readout sequence, but typically the first echo suffices. The readout sequence is phase-cycled similar to a CPMG (Carr-Purcell-Meiboom-Gill) sequence and the resultant echoes are co-added to eliminate instrumentation artifacts. As usual, the data points are corrected for environmental factors such as ambient temperature. The data points are fitted to a multi-exponential $T_1$ model, as known in the art. The $T_1$ times to be extracted ("bins") preferably are spaced on a logarithmic grid, such as the following example sequence: 1, 3, 10, 30, 100, 300, 1000, and 3000 ms. Although these happen to be the saturation-recovery times as well, such a one-to-one relationship is not necessary. Finally, in accordance with the method, the best-fit amplitudes for each bin are computed.

Next, the porosity ($\phi_{NMRA}$) is computed as the sum of all amplitudes for all $T_1$ bins. The resulted porosity is total porosity of water, oil and gas. In a specific embodiment, the Free Fluid Index (FFI) may then be computed as the sum of the amplitudes for $T_1$ greater than 50 ms (bins 100 ms and higher). Then, a difference between the total porosity $\phi_{NMRA}$ and the FFI is taken to determine the bound water porosity. In non-consolidated formations, which are characteristic to most drilling environments, only water-saturated shales are present, thereby the above-difference represents porosity associated with clay bound water (CBW).

Figure 12:
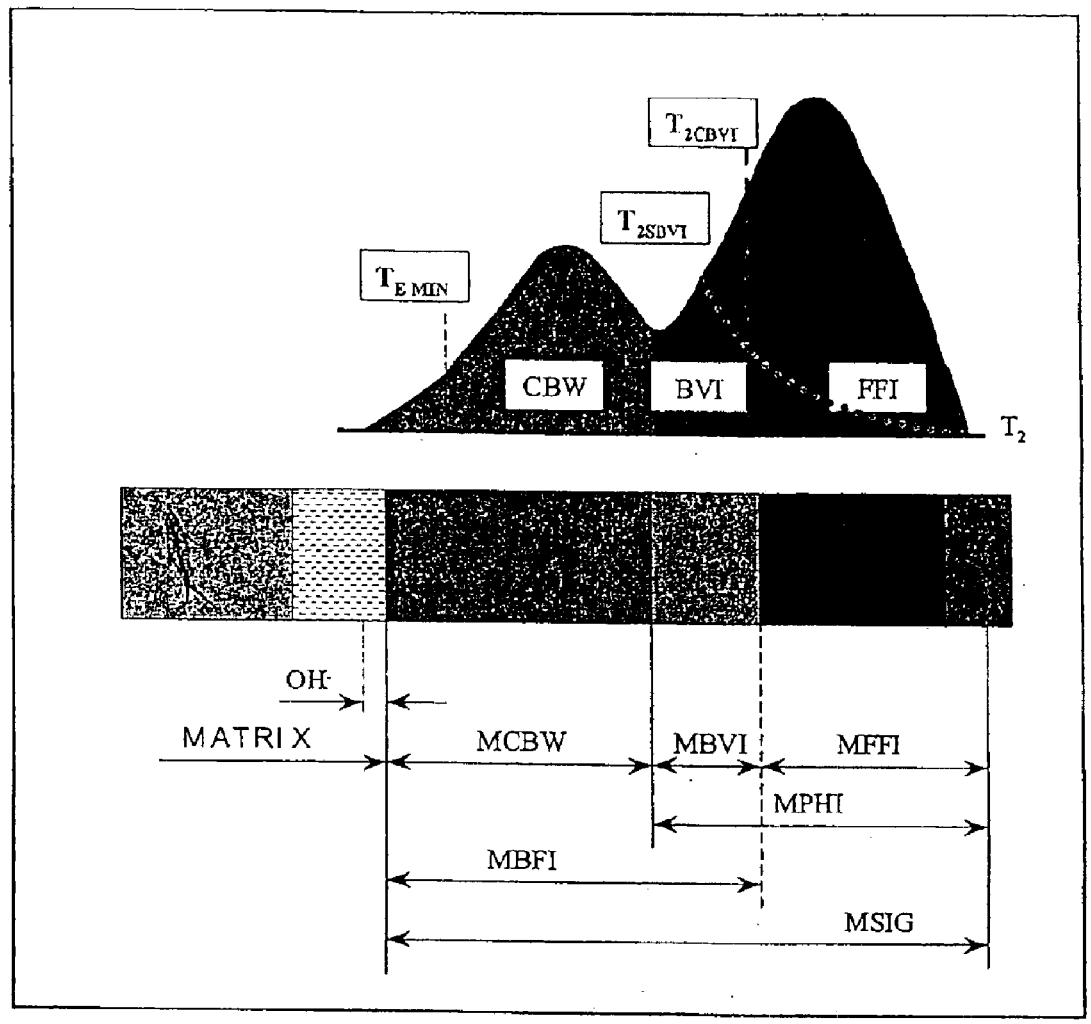
FIG. 12 illustrates an exemplary $T_2$ porosity distribution.

In accordance with another embodiment, the primary data record in $T_2$ mode is CPMG spin-echo amplitudes equivalent to those collected with the wireline tool using multiple wait times. The frequencies are advantageously, but not necessarily, programmable around a center frequency of about 500 kHz, with a minimum echo spacing ($T_E$) of 0.5 ms. The echo trains are phase-cycled and fitted to a $T_2$ model of decaying exponentials. Multiple wait times allow computation of echo differences, which are analyzed for the presence of oil and gas signatures. The procedure has been described in detail in the wireline logging literature and need not to be repeated in detail here. Final outputs include, for example: (1) $T_2$ Porosity, corrected for gas hydrogen density where appropriate; (2) $T_2$ Free Fluid, also corrected for gas hydrogen density; (3) $T_2$ Capillary Bound Water, which is derived from the $T_2$ distribution; (4) $T_2$ Clay-Bound Water, which is also extracted from the $T_2$ distribution. FIG. 12 illustrates a distribution of these porosity components on a typical $T_2$ curve, with break points identifying CBW, BVI and FFI porosities.

Figure 13:
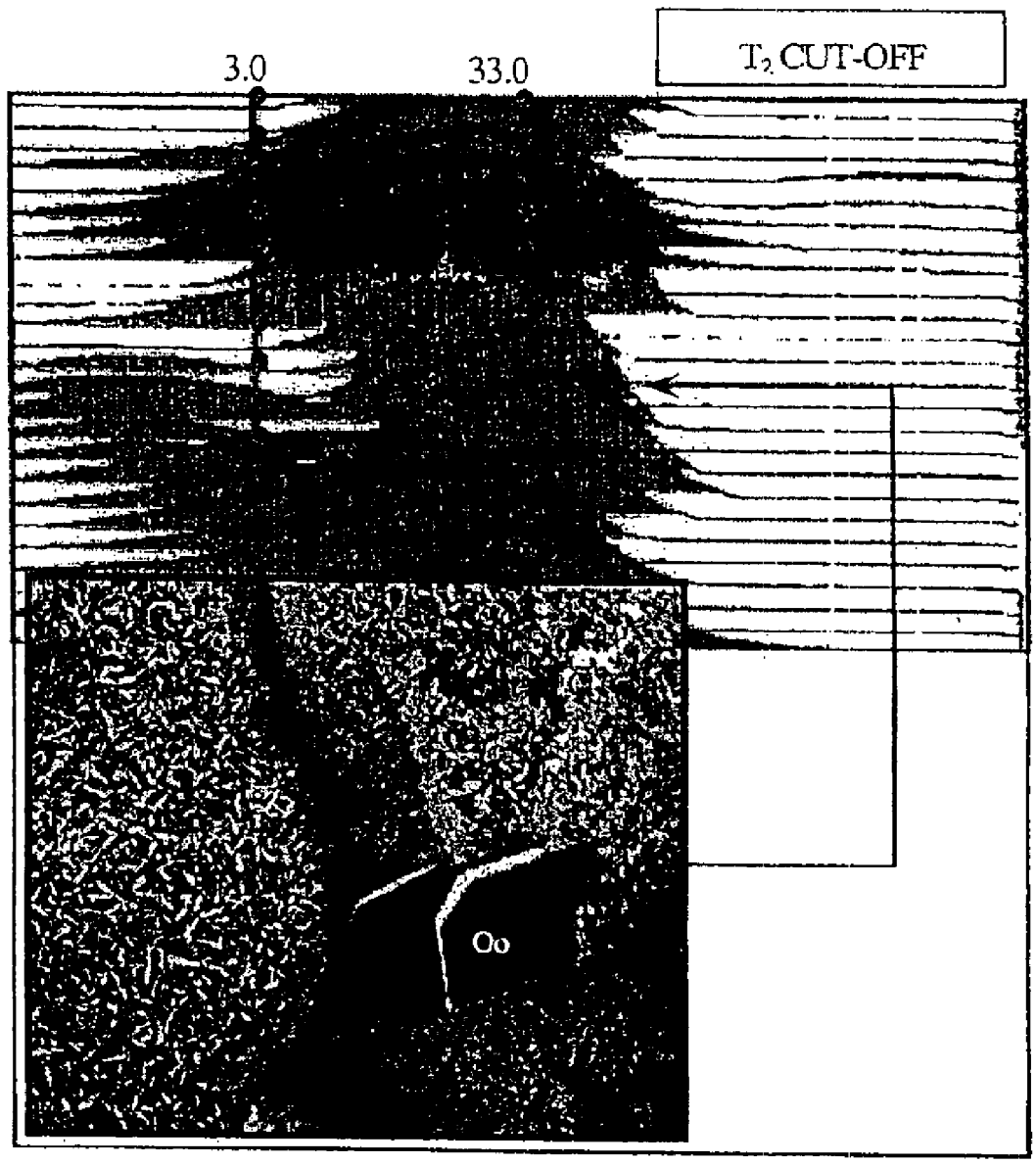
FIG. 13 illustrates NMR response in a rock sample.

With reference to FIG. 12, several methods are known in the art to determine the break point on a $T_2$ spectral porosity distribution curve. In one embodiment, a spectral BVI (SBVI) method may be used to determine the break points in the $T_2$ spectral porosity distribution. The method is based on the recognition that each pore can contain both free and bound fluids. More specifically, each pore size seen in the 100% brine-saturated spectra is assumed to contain some bound water. This is defined by a weighting function $W(T_{2,i})$, where $0 \leq W(T_{2,i}) \leq 1$, that defines the fraction of bound water associated with each pore size. Various methods for obtaining the weighted functions have been described in the wireline logging literature and need not to be repeated in detail here. For more information on the spectral BVI see, for example, Coates, G., Xiao, Lizhi, and Prammer, M. G., NMR logging principles and applications; Halliburton Energy Services, 1999;

In another embodiment of the present invention, cutoff BVI (CBVI) method is used to determine the break points on the $T_2$ spectral porosity distribution. The method is based on a fixed $T_2$ value ($T_{2cutoff}$) that divides the $T_2$ distribution into two components, one consisting of pore sizes containing bound water and the other consisting of pore sizes containing free fluids. In the absence of laboratory data, default values based on lithology are used for $T_{2cutoff}$. A $T_{2cutoff}$ of 33 ms is used for sandstones, and 90–100 ms for carbonates; these values, however, are also affected by several other factors, such as pore-wall chemistry, minor paramagnetic or ferromagnetic components, texture, pore throat to pore body ratios, and other factors not well understood. In the same manner, applying a fixed $T_2$ cut-off value of 3 ms identifies a micro-porosity associated with clay-sized particles. As seen from FIG. 13, which shows a sample of rock from Matagorda Island, the $T_{2cutoff}$ values of 3 ms and 33 ms separate clay bound and capillary/free volumes correctly.

In yet another embodiment, $T_{2cutoff}$ can be determined in the laboratory with NMR measurements on core samples. Core samples are analyzed for NMR characteristics at two saturation conditions, $S_w=100\%$ and (after establishing the appropriate value of saturation from a capillary-pressure curve, or directly desaturating the sample to the appropriate capillary pressure) $S_W$=irreducible. However, this approach provides measurements of total amount of irreducible fluids and does distinguish between clay- and capillary bound components. Various clay minerals exhibit wide range of relaxation times, some exceeding the commonly used 3 ms cut-off. For example, Prammer M. G., et al., in "Measurements of Clay-Bound Water and Total Porosity by Magnetic Resonance" the Log Analyst, 1996 37,#6,61 reported $T_2$ models at 2, 5 and 16 ms, respectively for clay-bound water in illite, chlorite and kaolinite, other published material gives different values.

It should be further noted that when certain parts of $T_2$ spectra are associated with clay or with intergranular porosity it is often assumed that pore sizes and distribution are proportionally related to the size and distribution of particles composing this rock. Thus, in clastic 100% water saturated environments good "clean" peak at large $T_2$ values is associated with good well-sorted pores, which is typically representative of a clean well-sorted medium-to-coarse grained sandstone. When, however, observed peak is shifted towards the faster $T_2$ components and become more widely "sagged", there is a good ground for interpreting such rock as a shaly fine-grained poor sorted sandstone. If that is true, then a one fixed cut-off of 3 ms separating our microporosity associated with clay-sized particles might not be valid; especially in the cases represented by a uni-modal $T_2$ distribution. Accordingly, in a preferred embodiment, minimum $T_2$ value is used to separate CBW and free-fluid (or effective) porosity for bi-modal distribution.

Furthermore, since NMR interpretation always utilize a various $T_{2cut-off}$ methods to discriminate free- and capillary-bound fluids, it is natural to investigate whether an additional cut-off exists which will separate clay bound water. Over past years several lab studies has been undertaken in that direction; some published results are summarized in the FIG. 11. These result show that in general clay minerals exhibit the decrease in their relaxation times ($T_2$) from kaolinite to chlorite, illite and smectite. The surface relaxivity of a clay is somewhat a function of clay's iron content, and hence mineralogy. Kaolinite would be expected to mainly affect the surface-to-volume ratio, whereas chlorite due to its iron content would also affect the surface relaxivity. The position of $T_{2cut-off}$ associated with the clays also depends on their distribution, i.e. rock diagenesis. But all exact values are descriptive rather than diagnostic, and there is no way that one single $T_{2cutoff}$ value will adequately describe the separation of clay bound porosity and free fluid porosity.

Figure 6:
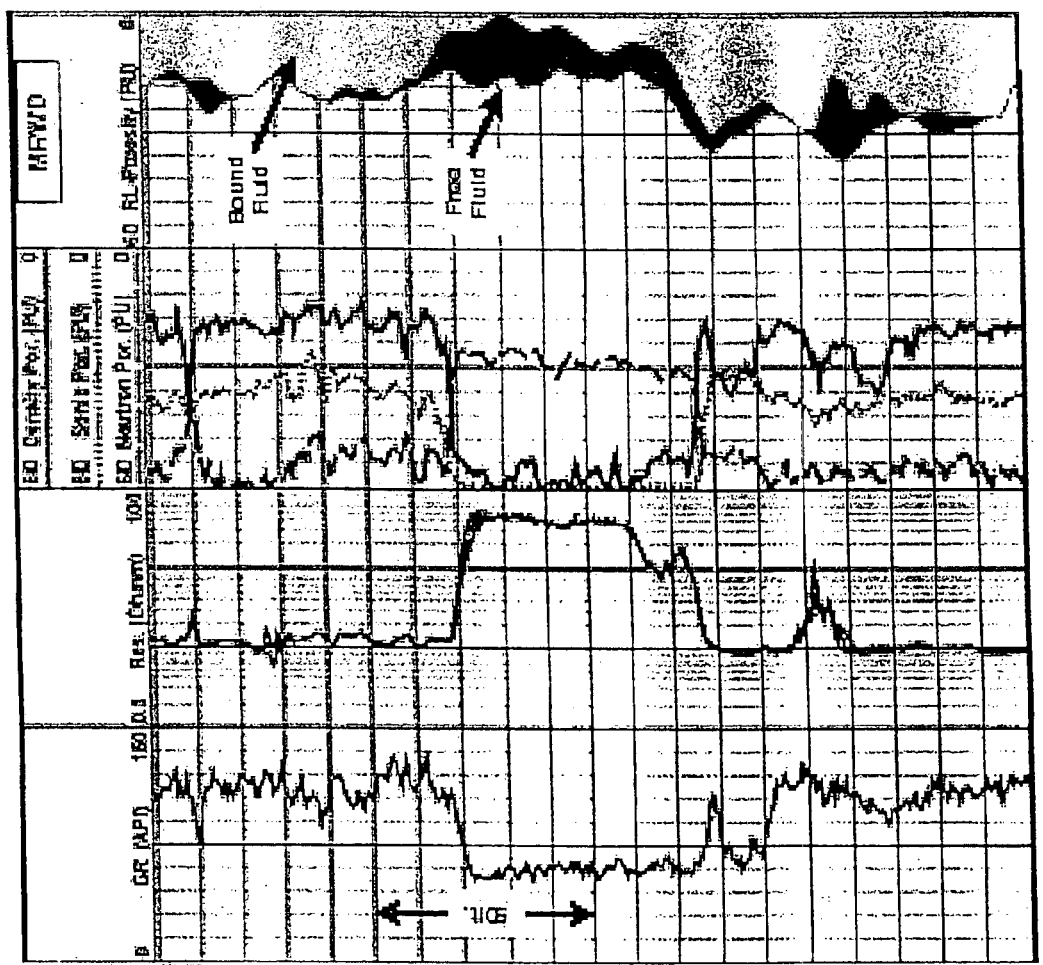
FIG. 6 represents a NMR-WD $T_1$ log from a deep-water exploration well.

FIG. 6 displays a small portion of a $T_1$ Log ($T_1$), in accordance with this invention, where all data points were acquired during the actual drilling operation of a deepwater exploration well. From left to right, the tracks contain the following curves: Track 1 shows LWD natural gamma ray; Track 2 displays LWD resistivity logs for four different depths of investigation (i.e., extra shallow, shallow, medium and deep); Track 3 shows sonic, neutron and density porosities; and Track 4 presents NMR-WD porosity (the free fluid portion is shaded in black, and the bound fluid portion is shaded in light gray). From the NMR log it is observed that the reservoir is clearly identifiable by the increase in free fluid volume. This reservoir contains gas, which explains the drop in neutron porosity and the very high reading in sonic and density porosities. The $\phi_{NMRA}$ porosity, however, undercalls true porosity due to the depressed hydrogen density of methane gas.

Figure 7:
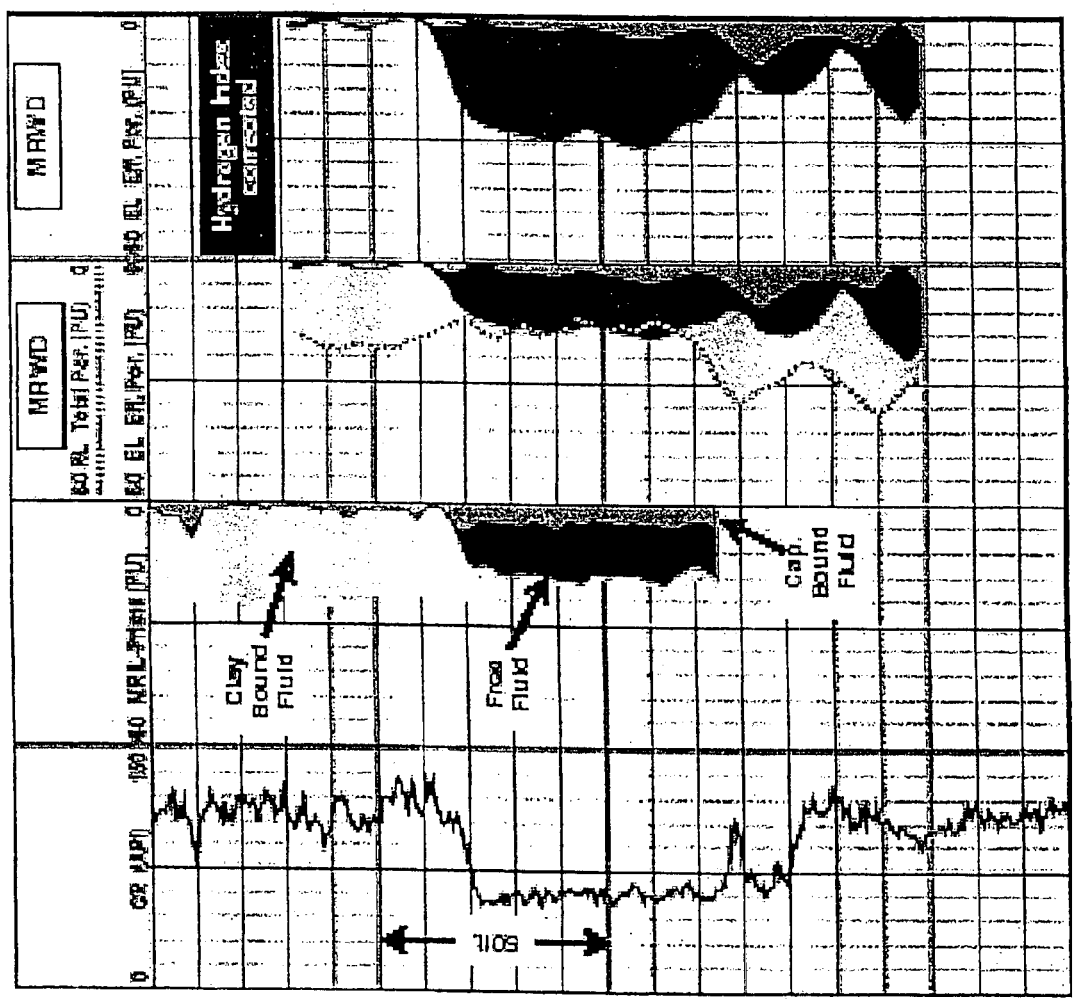
FIG. 7 represents a NMR-WD Evaluation log from the same reservoir as shown in FIG. 6.

For comparison, FIG. 7 shows an Evaluation Log acquired while wiping over the reservoir zone. Again, Track 1 shows natural gamma ray; Track 2 presents the reference MRIL-Prime™ wireline log (total porosity, capillary-bound fluid and clay-bound fluid); Track 3 shows $T_2$ effective porosity, $T_2$ free fluid and $T_2$ capillary-bound fluid. For comparison, $T_1$ porosity acquired while drilling is overlaid as dotted line. In Track 4, $T_2$ effective porosity and free fluid are shown corrected for the hydrogen index of methane gas for these reservoir conditions. As seen, the reservoir all results are very consistent.

The agreement of total porosity obtained during $T_1$ and effective porosity obtained during $T_2$ indicates two facts: (a) the reservoir is clean sand with little clay contents, and (b) the invasion profile did not substantially change between drilling, wiping, and wireline logging. In particular, above, but also below the reservoir zone, there is total porosity, but no or little effective porosity. In these intervals, fast relaxing clays with $T_2$ less than 1 ms are prevalent. Such fast relaxation times are not resolved by the 1.2 ms echo train used for the wiping log. The LWD measurement (echo spacing 0.5 ms), however, can detect fast clay components resulting in a correct total porosity reading.

Another known method for calculating bound water using NMR is the fixed cutoff method, which is described in U.S. Pat. No. 5,389,877, the contents of which are incorporated by reference. That reference describes using NMR techniques, in which a short train of spin echoes (i.e., j echoes) are used to obtain a sharp cutoff (i.e., the fixed cutoff relaxation time) that can be used to determine the producible volume in a borehole by measuring bound fluid and subtracting it from total porosity. They utilize a significantly shortened wait time tr, where tr is the time from the last 180° pulse of one NMR experiment until the application of the 90° pulse to start the next NMR experiment—where only single pulse sequences are utilized (e.g., while the drill pipe is moving), the shortened wait time is defined from the time the spins enter the static magnetic field. The shortened wait time is selected so that the static magnetic field is only applied for a short period of time before the next NMR experiment begins. This results in polarizing only the bound fluid in the formation, rather than the bound and free fluid, so that the measured amplitude represents the actual bound fluid volume of the part of the formation being analyzed.

(B) Pore Pressure from NMR data

The estimation or determination of pore fluid pressure is a major concern in any drilling operation. The pressure applied by the column of drilling fluid must be great enough to resist the pore fluid pressure in order to minimize the chances of a well blowout. Yet, in order to assure rapid formation penetration at an optimum drilling rate, the pressure applied by the drilling fluid column must not greatly exceed the pore fluid pressure. Likewise, the determination of horizontal and vertical effective stresses is important in designing casing programs and determining pressures due to drilling fluid at which an earth formation is likely to fracture.

The commonly-used techniques for making pore pressure determinations have relied on the use of overlay charts to empirically match well log data to drilling fluid weights used in a particular geological province. These prior art techniques are semi-quantitative, subjective and unreliable from well to well; none is soundly based upon physical principles.

Effective vertical stress and lithology are the principal factors controlling porosity changes in compacting sedimentary basins. Sandstones, shales, limestones, and others, compact at different rates under the same effective stress. An effective vertical stress log can be calculated from observed or calculated porosity for each lithology with respect to a reference curve for that lithology. Calculating pressure, and detecting abnormal pressure, is particularly beneficial while drilling through shales. Drilling through overpressured shales will not cause a large volume of low density fluid to enter the wellbore and displace drilling mud, because the permeability of the shales is too low. However, if a high permeability region with abnormal pressure, for example a typical sandstone reservoir, is encountered with underweighted drilling mud, low density fluid will enter the wellbore at increasing rates and the well might become uncontrollable.

Therefore, once the porosity and bound water volume of the shale formation has been determined, various techniques may be used to determine pressure deviations from the normal compaction trend. Such known techniques are described by (1) Hottmann et al. in "Estimation of Formation Pressures From Log-Derived Shale Properties" JPT (*Journal Petroleum Technology*), June 1965; (2) Eaton in "The Equation for Geopressure Prediction From Well Logs," paper SPE 5544, 1975 Annual Technical Conference, Dallas, September 28–October 1; (3) Rasmus et al. "A Framework To Estimate Pore Pressures in Real-Time," February 1990. Measurement-While-Drilling Symposium, Louisiana State University, Baton Rouge, La.; (4) Holbrook et al. in "A Petrophysical/Mechanical Mathematical Model for Real-Time Wellsite Pore-Pressure/Fracture-Gradient Prediction, Paper SPE 16666 presented at 1987 SPE Annual Technical Conference, Dallas, September; and (5) Bryant in "A Dual Shale Pore Pressure Detection Technique" paper SPE 18714 presented at the 1989 SPE/IADC Drilling Conference, New Orleans, La. Febuary–March. All of the above papers incorporated herein by reference and are familiar to those of ordinary skill in the art.

EXAMPLE 1

Ben Eaton's Method

Ben Eaton's method for pore and fracture pressure analysis is one of the most widely industry-accepted techniques. Particularly, it has proven to be extremely valuable in the Gulf-of-Mexico area. Two key equations, developed by Eaton, after modifications are as follows:

$$P_P = P_0 - \left[P_0 - 0.465 * \left(\frac{\varphi_{NMRN}}{\varphi_{NMRA}}\right)^E\right]$$

where:

$P_P$—pore pressure or formation pressure gradient in psi/f
$P_0$—overburden pressure in psi/f;
0.465—water gradient, suggested by B. Eaton for Gulf-of-Mexico;
$\phi_{NMRN}$—normalized NMR-porosity for given depth;
$\phi_{NMRA}$—apparent (measured) NMR-porosity for given depth;
E—Eaton coefficient, which was suggested to be 1.2 when resistivity data used and 3.0 for acoustic data; however later research indicate that depending on reservoir conditions, lithology, and the like this coefficient may vary from 1.2 to 5.0. Advantageously, an Eaton coefficient is determined for a region and utilizing NRM bound water porosity values.

Once the pore pressure has been computed the fracture pressure may be calculated as follows based on:

$$P_F = (P_0 - P_p) * \left(\frac{v}{1-v} + P_P\right)$$

where v—Poisson's ratio.

It should be noted that the overburden pressure at given depth (D[ft]) equals cumulative weight of the rocks above:

$$P_0 = 0.4335 \int_0^D \rho_b(D) dD$$

where 0.4335—is a conversion coefficient of g/cc into psi/f; and $\rho_b = \phi_{NMRA}\rho_W + (1-\phi_{NMRA})\rho_M$ i.e. function of porosity; w—water and m—matrix density. If no density information is available, as for example in the research conducted in Gulf-of-Mexico, studies allow calibrating changes in shale density vs. depth which could be approximated with the following exponents: $\rho_b = 0.2424 * \ln(D) + 0.23$ for consolidated formations, and $\rho_b = 0.1661 * \ln(D) + 0.84$ for unconsolidated formation.

Figure 8:
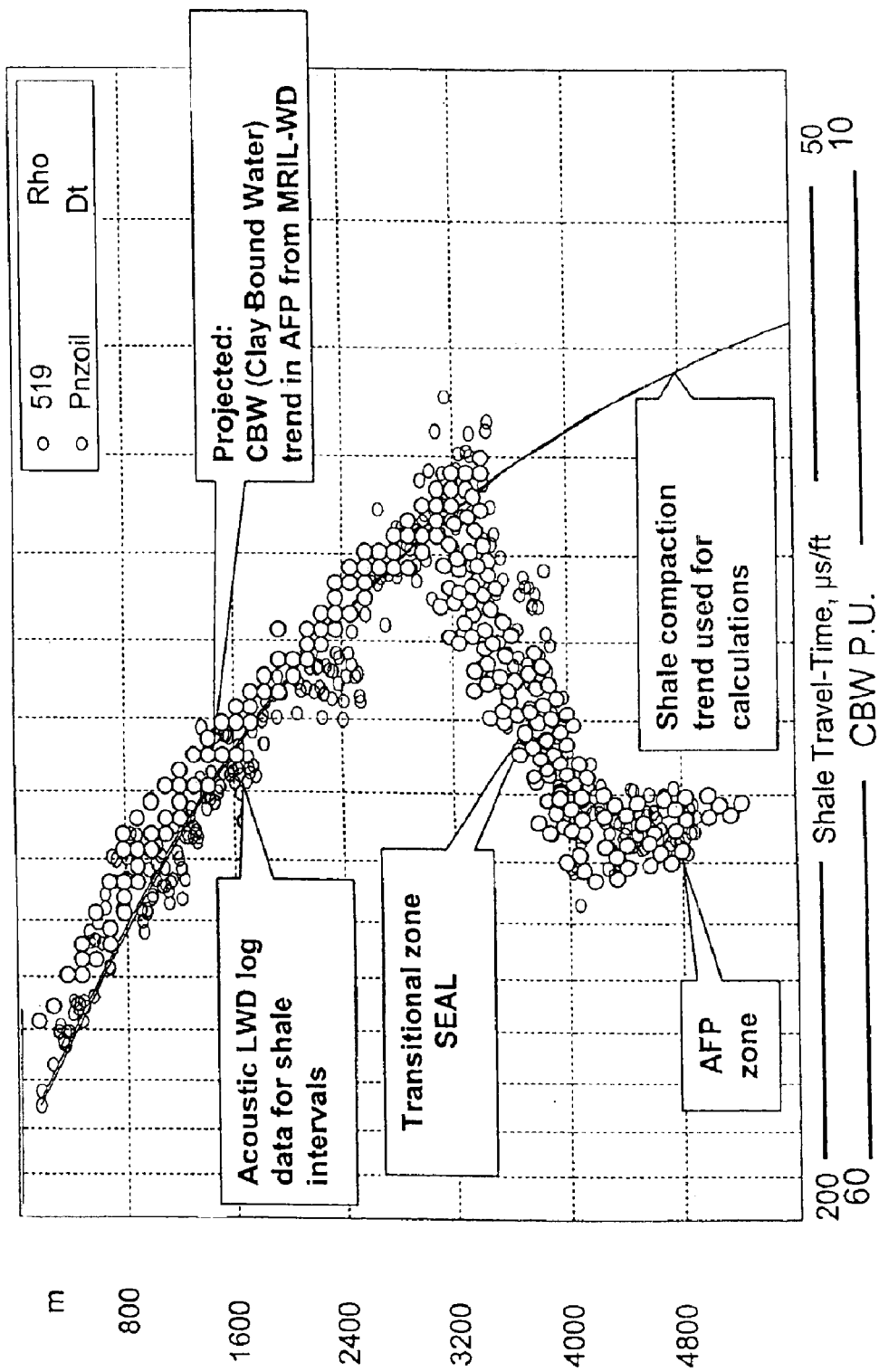
FIG. 8 illustrates comparison between NMR-WD porosity data and acoustic log data.

The overpressurized zones may be determined very accurately using $T_1$-derived porosity and Eaton's pressure analysis method. FIG. 8 presents comparison of acoustic LWD log for shale intervals and CBW trend from the NMR $T_2$ measurements in accordance with the preferred embodiment of the invention described above in Gulf-of-Mexico Matagorda Island. In this study, the acoustic logs are believed to have provided accurate results and there is a very good correlation between the acoustic logs and NMR measurements.

EXAMPLE 2

Equivalent Depth Method

Figure 9:
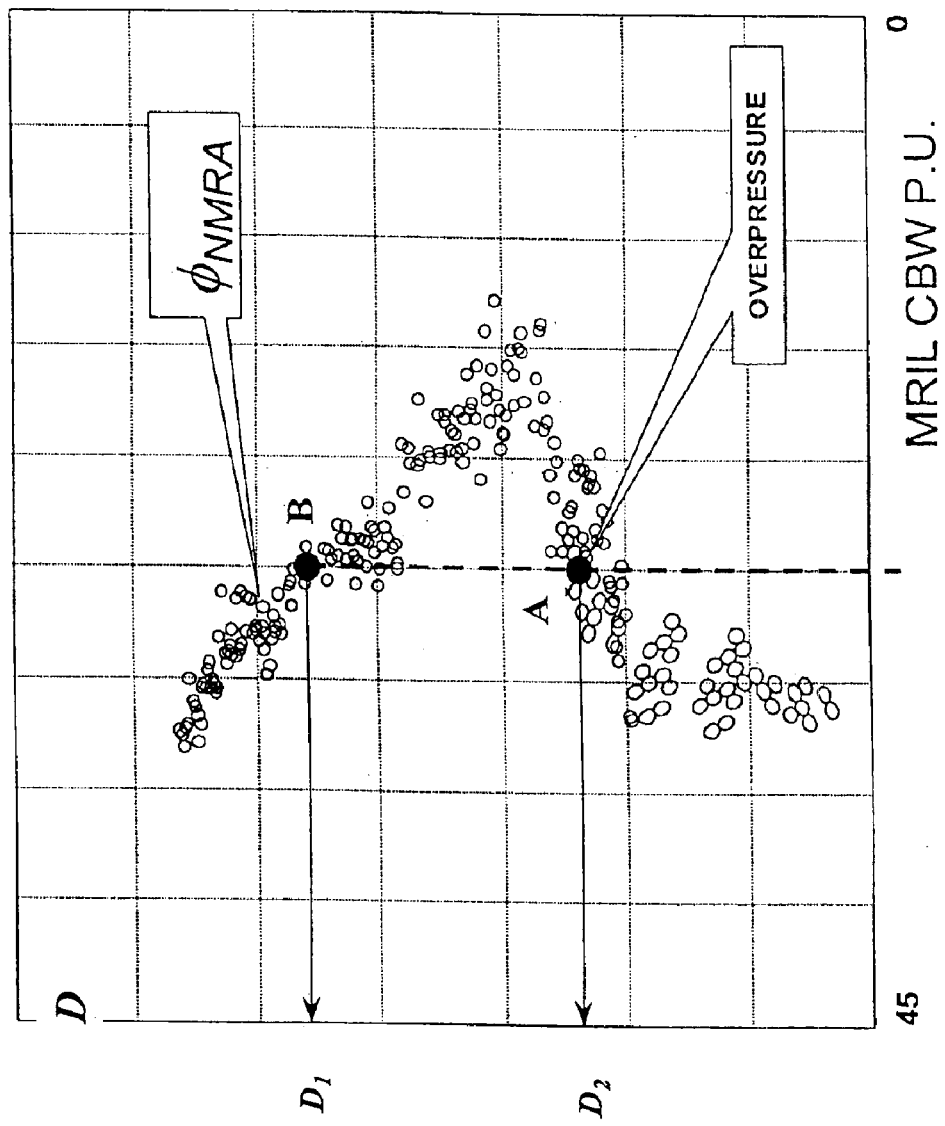
FIG. 9 illustrates a method for pressure prediction using Equivalent Depth Method.

Another known method for formation pressure analysis that can be used according to this invention is the Equivalent Depth Method. With reference to FIG. 9, the technique generally requires several steps: First, porosity $\phi_{NMRA}$ is plotted versus depth and a normal trend line is established. Second, a vertical line that intercepts the normal trend of NMR porosity is drawn. Third, depths at point of interest "A" and point of interception "B" are recorded. Fourth, a formation pressure at point "A", $P_p = D_1 - 0.535 D_2$, is calculated.

It should be noted that many pore and fracture pressure models require the use of shale values for compaction trend. Therefore, in accordance with a specific embodiment of the invention, the following parameter may be used as a shale indicator on spectral porosity data: for consolidated formations $$\frac{CBW}{BFI} \geq T_{1CUT-OFF},$$

and for non-consolidated formations $$\frac{CBW}{CBW + BVI} \geq T_{1CUT-OFF}.$$

The statistical studies of overpressured formations in the Gulf-of-Mexico suggest a value of the above-parameter of 0.85, however, it may vary between various formations.

Other methods or correlations are known and may be developed, which correlate the bound water content, and/or the porosity, of shale layers with the likelihood of overpressure, and these other methods or correlations are expected to be useful with this disclosed method. See, for example, U.S. Pat. No. 4,981,037, which is incorporated by reference. Furthermore, robust porosity measurements could be used in previously accepted pore pressure models or independently as an Equivalent Depth method.

This method enables recognition of the presence of gas and is not sensitive to induced fractures and/or changes in formation water salinity. It is possible to utilize data obtained from the $T_1$ measurements to deduce the presence of hydrocarbon-based hydrogen, for example by utilizing a different part of the spectral data, as is known in the art. The porosity data can be corrected for the presence of hydrocarbons, or alternately the data can be collected so that the contributions of the hydrogen associated with hydrocarbons is not a pertinent factor. Alternatively, the presence of hydrocarbons in a shale zone may, in some regions, itself be an indicator of overpressure in the underlying formations. Therefore, recognition of complex overpressured zones in Black Shales associated with liquid hydrocarbon generation also could be performed.

In sum, a novel NMR-based technique has been disclosed that allows determination of the normal compaction trend and calculation of overpressure in transition zones using $T_1$ real-time measurements. Most importantly, the NMR signal gives a "spectral" or incremental porosity, which allows the interpreter to separate the clay-bound water signal from the signal from capillary-bound/free fluids. The method of detecting overpressure can be based on the comparison of the clay-bound water porosity of shale zones, preferably shale zones that are separated vertically in a well by at least one permeable zone. Advantageously, this at least one permeable zone, i.e., permeability of at least one millidarcy, is normally pressured. The detection of overburden can be the result of anomalies in the normal clay-bound water in shale versus depth for a given well, or it can be a numerical calculation of pore pressure or other indicators that is/are based on correlations that have been shown to be reliable for a region. For example in a well drilled with a water-based mud, the presence of induced or tectonic fractures will "mislead" resistivity and acoustic logs. NMR on the other hand will discriminate between a signal from drilling mud in fractures (which will show-up in a BVI part of spectrum) and a micro-porosity associated with shales. For example, in wells drilled in the Bazenov formation (West Siberia, Russia), the presence of liquid hydrocarbons was a direct indicator of overpressure. Resistivity Logs could not have been used due to relative absence of water in the shales. Acoustic Logs were confusing due to extremely complex lithology (mixture of carbonate, siliceous material, dispersed organic matter and shales). Neutron logs read all hydrogen—even in the tar sections. In that case, NMR measurements were the only ones that allow evaluation of the formation for presence of liquid media and hence overpressure recognition in black shale formations.

A preferred novel NMR-WD-based technique that allows determination of the normal compaction trend and calculation of overpressure in transition zones, i.e., shale zones, uses $T_1$ real-time measurements to calculate the bound water fraction of shale porosity, and then incorporates this data into one of several known correlations to detect and calculate abnormal pressure.

(C) The NMR LWD Tool

Figure 10:
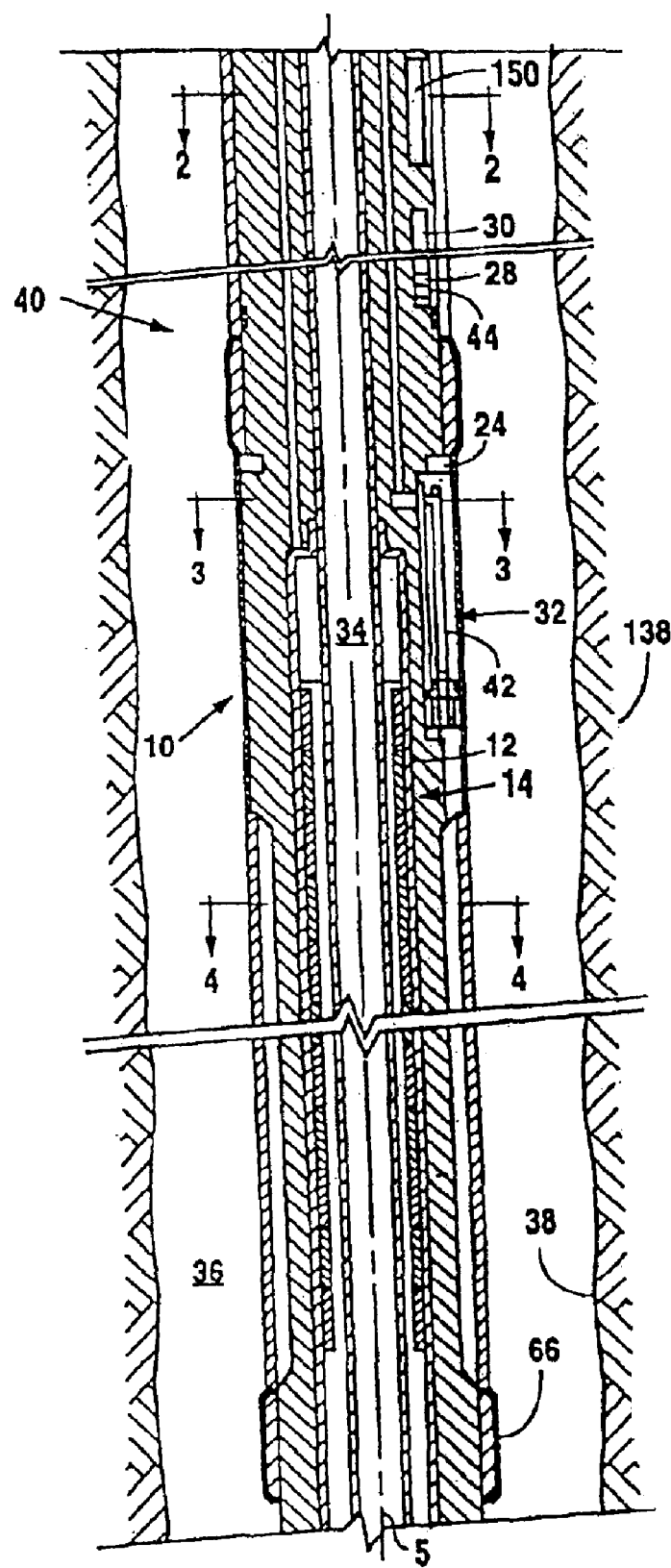
FIG. 10 illustrates diametrical cross-sectional views of the NMR logging apparatus.

In a preferred embodiment of the invention, a NMR tool having the mechanical strength and measurement sensitivity to perform NMR measurements of an earth formation while drilling a borehole is utilized. FIG. 10 illustrates an NMR WD tool 40 used and operated in accordance with a preferred embodiment of the present invention. NMR tool 40 comprises a nonmagnetic metal drill collar 10 that encloses a tubular, permanent magnet 12, which surrounds a mud tube 34 through which drilling mud may be pumped during the drilling of a borehole 36 into the earth formation 138. The tool 40 further comprises a stabilizer section 66, antenna 14, magnet section 12, capacitor compartment 32 with tuning capacitors 42, accelerometers 24, antenna driver 28, signal processor 30 and data transmitter 150.

Permanent magnet 12 has a magnetic field direction $B_0$ that is substantially perpendicular to the axis of the borehole. Collar 10 of a non-magnetic material, or of a substantially non-magnetic material, may beneficially surround magnet 12. At least one antenna 14 is positioned a distance from the permanent magnet, particularly outside the collar. Advantageously, a soft magnetic material is positioned in a predetermined relationship with the collar and the magnet that helps to shape the magnetic field of the tool 40. Due to the non-magnetic collar 10, the tool 40 can withstand the extreme conditions in the borehole environment while the borehole is being drilled. Motion management apparatus and method are beneficially employed to identify time periods when the NMR measurements can be taken without the accuracy of the measurement being affected by the motion of the tool or its spatial orientation.

While characteristics of a tool in a preferred embodiment have been presented, other tools are known and can be used to characterize formation properties in the process of predicting overpressure, including those tools described in U.S. Pat. No. 5,923,167, U.S. Pat. No. 6,111,408; U.S. Pat. No. 6,173,793; U.S. Pat. No. 6,204,663; U.S. Pat. No. 6,242,912; U.S. Pat. No. 6,242,913; U.S. Pat. No. 6,255,819; U.S. Pat. No. 6,268,726; U.S. Pat. No. 6,316,940; U.S. Pat. No. 6,337,568; U.S. Pat. No. 6,362,619, U.S. Pat. No. 6,366,087; U.S. Pat. No. 6,411,087; U.S. Pat. No. 6,446,736; U.S. Pat. No. 6,518,756; U.S. Pat. No. 6,531,868; and U.S. Pat. No. 6,541,969, which are incorporated herein by reference.

Processing of NMR data is done in software, hardware or a suitable combination preferably capable of real-time data manipulation. Naturally, the selected processing mechanism can be programmed to implement the above described abnormal pressure zones automatically. In the alternative, porosity data from the tool can be displayed to a human operator who can make a decision regarding abnormal pressure zones based thereon.

While the foregoing has described and illustrated aspects of various embodiments of the present invention, those skilled in the art will recognize that alternative components and techniques, and/or combinations and permutations of the described components and techniques, can be substituted for, or added to, the embodiments described herein. It is intended, therefore, that the present invention not be defined by the specific embodiments described herein, but rather by the appended claims, which are intended to be construed in accordance with the following well-settled principles of claim construction.

What we claim is:

1. A method for nuclear magnetic resonance (NMR) logging of a geologic formation comprising the steps of:
    a. providing a plurality of NMR measurements over a depth interval of the geologic formation;
    b. computing from the NMR measurements a plurality of porosity values corresponding to the depth interval of the geologic formation;
    c. processing the computed porosity values to detect abnormal formation pressure in a zone within the depth interval.

2. The method of claim 1, wherein the NMR measurements data is obtained from a logging-while-drilling NMR tool.

3. The method of claim 2, wherein the plurality of porosity values are obtained from one or more NMR $T_1$ relaxation curves.

4. The method of claim 1, wherein the depth interval of the geologic formation is dimensioned to contain multiple zones, including at least one normally pressured zone.

5. The method of claim 3, wherein the one or more $T_1$ relaxation curves is processed to extract the dominant $T_1$ relaxation modes, and the method further comprises providing estimates of the amounts of clay-bound water, free water, and hydrocarbons.

6. The method of claim 1, wherein the provided plurality of NMR measurements comprises one or both of $T_1$ and $T_2$ NMR measurements.

7. The method of claim 6 further comprising the step of obtaining at least one of electric, acoustic, and nuclear log data, and plotting the data as a function of depth to provide a normal compaction trend.

8. The method of claim 1, wherein NMR measurement data is collected by applying a saturation pulse and a readout sequence applied after a timed recovery delay.

9. The method of claim 8, wherein the time between applying a readout sequence and measuring an echo signal is about 0.5 ms.

10. The method of claim 8, wherein the recovery delay varies between about 1 and at least about 30 ms.

11. The method of claim 8, wherein the recovery delay varies between about 1 and at least about 1000 ms.

12. The method of claim 1, wherein an abnormally pressured zone is determined using NMR $T_1$-derived clay-bound water porosity and porosity versus pore pressure correlation information.

13. The method of claim 12, wherein the pressure within the abnormally pressured zone is determined using $T_1$-derived porosity and Eaton's pressure analysis method.

14. The method of claim 1, wherein calculating clay-bound water using NMR is performed according to a fixed cutoff method.

15. A method for nuclear magnetic resonance (NMR) logging of a geologic formation comprising the steps of:
   a. lowering a NMR logging tool into a borehole;
   b. conducting NMR measurements of at least two zones of the geologic formation, the measurements comprising either a $T_1$ or $T_2$ relaxation spectra or a combination thereof;
   c. estimating clay-bound water volumes associated with the at least two zones of the geologic formation;
   d. processing the estimated clay-bound water volumes to detect abnormal formation pressure.

16. The method of claim 15, wherein steps (a)–(d) are performed while drilling the borehole.

17. The method of claim 15, wherein an indication of an abnormal pressure in a borehole zone is provided to a human operator.

18. The method of claim 15 further comprising the step of determining a normal compaction trend.

19. An apparatus for nuclear magnetic resonance (NMR) logging of a geologic formation comprising:
   a. means for providing a plurality of NMR measurements over a depth interval of the geologic formation;
   b. means for computing from the NMR measurements a plurality of porosity values corresponding to the depth interval of the geologic formation; and
   c. means for processing the computed porosity values to detect abnormal formation pressure in a zone within the depth interval.

20. The apparatus of claim 19, wherein the means for providing a plurality of NMR measurements comprises an NMR logging while drilling tool.

21. The apparatus of claim 19, wherein the NMR measurements comprise either a $T_1$ or $T_2$ relaxation spectra or a combination thereof.

* * * * *